United States Patent [19]
Varney et al.

[11] Patent Number: 5,608,082
[45] Date of Patent: Mar. 4, 1997

[54] COMPOUNDS USEFUL AS ANTIPROLIFERATIVE AGENTS AND GARFT INHIBITORS

[75] Inventors: Michael D. Varney, Carlsbad; William H. Romines, San Diego, both of Calif.

[73] Assignee: Agouron Pharmaceuticals, Inc., La Jolla, Calif.

[21] Appl. No.: 281,639

[22] Filed: Jul. 28, 1994

[51] Int. Cl.$^6$ ..................... C07D 333/10; C07D 333/22
[52] U.S. Cl. ................................. 549/70; 549/73
[58] Field of Search ........................... 549/70, 73

[56] References Cited

U.S. PATENT DOCUMENTS

| | | | |
|---|---|---|---|
| 4,590,203 | 5/1986 | Binder et al. | 514/397 |
| 4,684,653 | 8/1987 | Taylor et al. | 514/258 |
| 4,831,037 | 5/1989 | Taylor et al. | 514/258 |
| 4,845,216 | 7/1989 | Taylor et al. | 514/258 |
| 4,871,746 | 10/1989 | Taylor et al. | 514/258 |
| 4,882,333 | 11/1989 | Shih et al. | 514/258 |
| 4,882,334 | 11/1989 | Shih et al. | 514/258 |
| 4,883,799 | 11/1989 | Taylor et al. | 514/258 |
| 4,889,859 | 12/1989 | Taylor et al. | 514/258 |
| 4,895,946 | 1/1990 | Taylor et al. | 514/258 |
| 4,927,828 | 5/1990 | Taylor et al. | 514/258 |
| 4,988,813 | 1/1991 | Taylor et al. | 544/279 |
| 5,026,851 | 6/1991 | Taylor et al. | 544/279 |
| 5,217,974 | 6/1993 | Grindey et al. | 514/260 |
| 5,223,503 | 6/1993 | Gossett et al. | 514/258 |

FOREIGN PATENT DOCUMENTS

| | | |
|---|---|---|
| 438261 | 7/1991 | European Pat. Off. . |
| 593286 | 4/1994 | European Pat. Off. . |
| WO92/05153 | 4/1992 | WIPO . |
| WO94/13295 | 6/1994 | WIPO . |

OTHER PUBLICATIONS

Moran, "Folate antimetabolites inhibitory to de novo purine synthesis," New Drugs, Concepts and Results in Cancer Chemotherapy, Muggia (ed.), Kluwer Academic Publishers, Boston (1992), 65–87.

Young et al., "An Antibody Probe to Determine the Native Species of Glycinamide Ribonucleotide Transformylase in Chicken Liver," Biochemistry, vol. 23 (1984), 3979–3986.

Morrison, "Kinetics of the Reversible Inhibition of Enzyme- Catalysed Reactions by Tight–Binding Inhibitors," Biochem. Biophys. Acta, 185 (1969), 269–286.

Totani et al., "Synthesis of a Novel 5–Deaza–5–thia Analogue of Tetrahydrofolic Acid . . . ," J. Chem. Soc. Perkin Trans. 1 (Apr. 1974), 833–836.

Mosmann, "Rapid Colorimetric Assay for Cellular Growth and Survival . . . ," J. Immunol. Methods, vol. 65 (1983), 55–63.

Sako et al., "New and Facile Synthesis of 5,6,7, 8–Tetrahydro–5–deaza–5–thiapterins . . . ," Chem. Pharm. Bull., vol. 42, No. 4 (1994), 806–810.

Antony, "The Biological Chemistry of Folate Receptors," Blood, The Journal of the American Society of Hematology, vol. 79, No. 11 (1992), 2807–2820.

Pizzorno et al., "5, 10–Dideazatetrahydrofolic Acid (DDATHF) Transport in CCRF–CEM and MA104 Cell Lines," The Journal of Biological Chemistry, vol. 268, No. 2 (1993), 1017–1023.

Alati et al., "Evaluation of the Mechanism(s) of Inhibition of the Toxicity, but not the Antitumor Activity of Lometrexol . . . ," Proceedings of the Am. Assoc. for Cancer Res., Abstract 2432, vol. 33 (1992), 407.

Shih et al., "Synthesis and Biological Activity of Acyclic Analogues of 5,10–Dideaza–5,6,7,8–tetrahydrofolic Acid," J. Med. Chem., vol. 35 (1992), 1109–1116.

Nemec et al., "The Synthesis of 4–Substituted 2–Thiophenecarboxylic Acids," Collection Czechoslov. Chem. Commun., vol. 39 (1974), 3527–3531.

Taylor et al., "Convergent and Efficient Palladium–Effected Synthesis of . . . (DDATHF)," J. Org. Chem., vol. 54, No. 15 (1989), 3618–3624.

Habeck et al., "A Novel Class of Monoglutamated Antifolates Exhibits Tight–binding Inhibition of Human Glycinamide Ribonucleotide Formyltransferase and Potent Activity Against Solid Tumors," Cancer Research, vol. 54 (Feb. 15, 1994), 1021–1026.

Hallberg et al, "On the Vilsmeier formylation of some methoxythiophenes," Chemical Abstracts, vol. 94, entry 94:156661, 1980.

Clarke et al, "Condensed isothiazoles. Part 5. Thieno[2,3–d] isothiazoles and thien[3,2–d]isothiazoles," Chemical Abstracts vol. 93, 93:95174, 1980.

*Primary Examiner*—Matthew V. Grumbling
*Attorney, Agent, or Firm*—Finnegan, Henderson, Farabow, Garrett & Dunner, L.L.P.

[57] ABSTRACT

Compounds of the Formula I, which are in equilibrium with their 4-hydroxy tautomers and are in the form of diastereomeric mixtures, and their pharmaceutically acceptable salts are potent GARFT inhibitors:

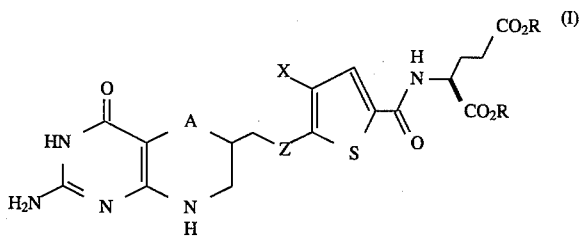

wherein A, Z, X, and $R_1$ and $R_2$ are defined in the specification. These compounds and their salts are useful as antiproliferative agents. The invention also pertains to pharmaceutical compositions and methods employing such compounds as GARFT inhibitors or antiproliferative agents. The invention also relates to compounds useful as intermediates for preparing such compounds, and to their synthesis.

11 Claims, No Drawings

COMPOUNDS USEFUL AS ANTIPROLIFERATIVE AGENTS AND GARFT INHIBITORS

BACKGROUND OF THE INVENTION

The present invention relates to compounds of the Formula I defined below, which inhibit the enzyme glycinamide ribonucleotide formyl transferase (GARFT). The invention also relates to pharmaceutical compositions containing the compounds of the Formula I, to their use to inhibit GARFT and to their use to inhibit the growth and proliferation of the cells of higher organisms or microorganisms such as bacteria, yeast and fungi. The invention also relates to the preparation of these compounds, and to intermediates used in their preparation.

GARFT is a folate dependent enzyme in the de novo purine biosynthesis pathway. This pathway is critical to cell division and proliferation. Shutting down this pathway is known to have an antiproliferative effect, in particular, an antitumor effect. Thus, a number of folate analogs have been synthesized and studied for their ability to inhibit GARFT. A prototypical specific tight-binding inhibitor of GARFT, 5,10-dideazatetrahydrofolic acid (DDATHF), has been reported to show antitumor activity. See F. M. Muggia, "Folate antimetabolites inhibitor to de novo purine synthesis," *New Drugs, Concepts and Results in Cancer Chemotherapy*, Kluwer Academic Publishers, Boston (1992), 65–87.

The large class of antiproliferative agents includes antimetabolite compounds. A particular subclass of antimetabolites known as antifolates or antifoles are antagonists of the vitamin folic acid. Typically, antifolates closely resemble the structure of folic acid and incorporate the characteristic P-benzoyl glutamate moiety of folic acid. The glutamate moiety of folic acid takes on a double negative charge at physiological pH, and therefore this compound and its analogs have an active energy driven transport system to cross the cell membrane and exert a metabolic effect. Research by a number of investigators has show that folic acid in both its reduced and oxidized forms and its analogs are actively transported into cells by at least two distinct transport mechanisms. These transport proteins are referred to as the reduced folate transport protein, which has a preference for reduced folates but will transport a number of folic acid derivatives. Methotrexate (MTX) is transported via the reduced folate transport system. The other folate transport protein is referred to as the membrane folate binding protein or mFBP, which has a preference for folic acid. See A. C. Antony, "The Biological Chemistry of Folate Receptors," *Blood, The Journal of the American Society of Hematology*, vol. 79 (1992), 2807–2820.

The anticancer glutamate-containing antifolates used clinically to date, including MTX, enter cells via the reduced folate transport system with one notable exception. 5,10-Dideazatetrahydrofolic acid (DDATHF) is an antitumor GARFT inhibitor currently undergoing clinical study. DDATHF has been shown to be transported into cells via both the reduced folate transport system and the mFBP. See G. Pizzorno et al., "5,10-Dideazatetrahydrofolic Acid (DDATHF) Transport in CCRF-CEM and MA104 Cell Lines," *The Journal of Biological Chemistry*, vol. 268 (1993), 1017–1023.

It has been suggested that undesirable toxicity, particularly in folate-depleted mammals, is related to the fact that DDATHF, a prior art GARFT inhibitor, has a high affinity for the mFBP, which is unregulated during times of folate deficiency. It has been further suggested that folic acid and other molecules that block the mFBP from transporting other GARFT inhibitors can attenuate the toxicity of such inhibitors. See, e.g., T. Alati et al., "Evaluation of the Mechanism(s) of Inhibition of the Toxicity, But Not the Antitumor Activity of Lometrexol (DDATHF) by Folic Acid," *Proceedings of the American Association for Cancer Research*, vol. 33 (1992), Abstract 2432, 407; L. L. Habeck et al., "A Novel Class of Monoglutamated Antifolates Exhibits Tight-binding Inhibition of Human Glycinamide Ribonucleotide Formyltransferase and Potent Activity against Solid Tumors," *Cancer Research*, vol. 54 (1994), 1021–1026; and U.S. Pat. No. 5,217,974 to Grindey et al.

SUMMARY OF THE INVENTION

Thus, an object of this invention is to produce compounds that are potent GARFT inhibitors having reduced toxicity. This object has been achieved through the antiproliferative agents of the Formula I below that are potent GARFT inhibitors but do not have tight binding to the mFBP. These compounds preferably have binding constants to the mFBP of at least a factor of 1000 less than DDATHF, yet still retain the favorable properties of GARFT inhibition and reduced folate transport for antitumor activity.

As indicated above, compounds of the invention possess antiproliferative activity, a property which can express itself in the form of antitumor activity. A compound of the invention can be active per se, or as a precursor converted in vivo to an active compound. Preferred compounds of the invention are especially active in inhibiting the enzyme GARFT. Particularly preferred compounds are active in inhibiting the growth of the L1210 cell line, a mouse leukemia cell line that can be grown in tissue culture. Compounds of the invention can also be active in inhibiting the growth of bacteria such as *Escherichia coli* gram-negative bacteria which can be grown in culture.

The compounds according to the invention, as well as the pharmaceutically acceptable salts thereof, may be incorporated into convenient dosage forms, such as capsules, tablets and injectable preparations. Solid or liquid pharmaceutically acceptable carriers, diluents or excipients may also be employed.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline solution and water.

The carrier or diluent may include any prolonged-release material, such as glyceryl monostearate or glyceryl distearate, alone or with wax. When a liquid carrier is used, the preparation may be in the form of a syrup, elixir, emulsion, soft gelatin capsule, sterile injectable liquid (e.g. solution) or a nonaqueous or aqueous liquid suspension.

The pharmaceutical preparations are prepared following conventional techniques of the pharmaceutical chemist involving steps such as mixing, granulation and compressing when necessary for tablet forms, or mixing, filling and dissolving the ingredients as appropriate to give the desired products for oral, parenteral, topical, intravaginal, intranasal, intrabronchial, intraocular, intraaural or rectal administration.

The compositions of the invention may further comprise one or more other pharmaceutically active compounds. For example, one of the following antitumor agents may be included in the composition: mitotic inhibitors (e.g., vinblastine); alkylating agents; dihydrofolate reductase inhibitors or TS inhibitors; antimetabolites (for example, 5-fluorouracil, cytosinerabinoside); intercalating antibiotics (for example, adriamycin, bleomycin); enzymes (for example, asparaginase); topoisomerase inhibitors (for example, etoposide); and biological response modifiers (for example, interferon). The compounds of the invention may also be used in combination with one or more antiproliferative agents or GARFT inhibitors, such as a compound described in commonly assigned International Publication No. WO 94/13295, published Jun. 23, 1994, or International Publication No. WO 92/05153, published Apr. 2, 1992, the disclosures of which are incorporated by reference herein. The compositions of the invention may also comprise one or more antibacterial, antifungal, antiparasitic, antiviral, antipsoriatic or anticoccidial agents. Exemplary antibacterial agents include: sulfonamides, such as sulfamethoxazole, sulfadiazine, sulfameter and sulfadoxine; dihydrofolic reductase inhibitors, such as trimethoprim, bromodiaprim and trimetrexate; penicillins; cephalosporins; and the quinolone carboxylic acids and their fused isothiazolo analogs.

Another aspect of the invention relates to a therapeutic method of inhibiting the growth or proliferation of cells of higher organisms or microorganisms, which comprises administering to a host an effective amount or quantity of a compound according to the present invention. The compounds of the invention are particularly useful in the treatment of mammalian hosts, such as human hosts, and in the treatment of avian hosts. A particularly preferred therapeutic process comprises administering to a host an amount of a compound according to the present invention effective to inhibit GARFT.

Many of the antiproliferative compounds described herein and their pharmaceutically acceptable salts thereof can be employed in the therapeutic process of the invention. The compounds may be administered in the form of a pharmaceutically acceptable composition comprising a diluent or carrier as described above.

A dose of a composition contains at least an effective quantity of the active compound and preferably is made up of one or more pharmaceutical dosage units. An "effective quantity" means a quantity sufficient to inhibit the folate metabolic pathways and derive the beneficial effects therefrom, e.g., through administration of one or more of the pharmaceutical dosage units.

An exemplary daily dose for a vertebrate host comprises an amount of up to one gram active compound per kilogram of the host, preferably one-half of a gram, more preferably 100 milligrams, and most preferably, about 50 milligrams or less, per kilogram of the host's body weight. The selected dose may be administered to a warmblooded animal or mammal, for example, a human patient in need of treatment mediated by folate metabolic pathways inhibition, by any suitable method of administrating the dose including: topically, for example, as an ointment or cream; orally; rectally, for example, as a suppository; parenterally by injection; or continuously by intravaginal, intranasal, intrabronchial, intraaural or intraocular infusion.

The compounds according to the invention produce any one or more of an antiproliferative effect, an antibacterial effect, an antiparasitic effect, an antiviral effect, an antipsoriatic effect, an antiprotozoal effect, an anticoccidial effect, an antiinflammatory effect, an immunosuppressive effect and an antifungal effect. The compounds are especially useful in producing an antitumor effect in a vertebrate host harboring a tumor.

DETAILED DESCRIPTION OF THE INVENTION AND PREFERRED EMBODIMENTS

In particular, the invention relates to compounds of the Formula I:

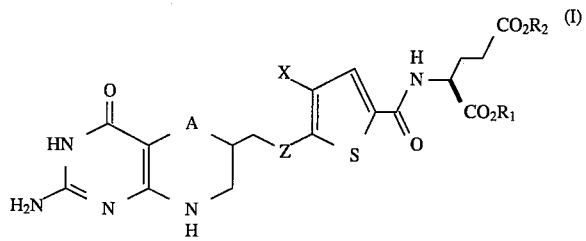

wherein:

A is sulfur, $CH_2$ or selenium;

Z is a substituted or unsubstituted $C_1$–$C_3$ alkyl group, a substituted or unsubstituted $C_2$–$C_3$ alkenyl group, a substituted or unsubstituted $C_2$–$C_3$ alkynyl group, a substituted or unsubstituted amino group, sulfur or oxygen;

X is a substituted or unsubstituted $C_1$–$C_6$ alkyl group; a substituted or unsubstituted $C_2$–$C_6$ alkenyl group; a substituted or unsubstituted $C_2$–$C_6$ alkynyl group; —C(O)E, wherein E is hydrogen, a substituted or unsubstituted $C_1$–$C_3$ alkyl group, a substituted or unsubstituted $C_2$–$C_3$ alkenyl group, a substituted or unsubstituted $C_2$–$C_3$ alkynyl group, a substituted or unsubstituted $OC_1$–$C_3$ alkoxy group, or $NR_{10}R_{11}$, wherein $R_{10}$ and $R_{11}$ are independently selected from hydrogen, substituted and unsubstituted $C_1$–$C_3$ alkyl groups, substituted and unsubstituted $C_2$–$C_3$ alkenyl groups, substituted and unsubstituted $C_2$–$C_3$ alkynyl groups; $NR_{10}R_{11}$, wherein $R_{10}$ and $R_{11}$ are independently defined as set forth above; hydroxyl; nitro; $SR_{12}$, wherein $R_{12}$ is hydrogen, a substituted or unsubstituted $C_1$–$C_6$ alkyl group, a substituted or unsubstituted $C_2$–$C_6$ alkenyl group, or a substituted or unsubstituted $C_2$–$C_6$ alkynyl group; cyano; or a substituted or unsubstituted $O(C_1$–$C_3)$ group; and $R_1$ and $R_2$ are each independently hydrogen or a moiety that forms (together with the attached $CO_2$) a readily hydrolyzable ester group.

The invention also relates to pharmaceutically acceptable salts of the compounds of Formula I.

Although the compounds of the Formula I are shown in the 4-oxo form and are referred to as such throughout this description, the oxo group exists in tautomeric equilibrium with the corresponding 4-hydroxy group. It will therefore be understood that the compounds of the Formula I include the structurally depicted 4-oxo and the tautomeric 4-hydroxy forms. Thus, the invention also relates to pharmaceutically acceptable salts of the 4-hydroxy tautomers of the compounds depicted by Formula I.

The compounds of the Formula I are in the form of diastereomeric mixtures. It will be understood that unless indicated otherwise, the compounds having chiral centers are in the form of mixtures of diastereomers.

Preferably, A is sulfur or $CH_2$.

When Z is substituted, the substituents are preferably selected from $C_{1-6}$ alkoxyl, $C_{1-6}$ alkyl and $C_{2-6}$ alkenyl such as vinyl, $C_{2-6}$ alkynyl, acyl such as formyl and acetyl, halogen, amino, hydroxyl, nitro, mercapto, monocyclic carbocycle, monocyclic heterocycle, nonfused polycyclic carbocycle, nonfused polycyclic heterocycle, hydroxy $C_{1-6}$ alkyl such as hydroxymethyl, and $C_{1-6}$ alkoxy $C_{1-6}$ alkyl. Preferably, Z is $CH_2$, $CH_2CH_2$, NH, oxygen, sulfur, $CH(CH_2OH)$ or $NCH_3$. More preferably, Z is $CH_2$.

When X is substituted, the substituents are preferably selected from OH, $NH_2$, O-methyl, O-ethyl, SH, $SCH_3$ and NH-methyl. Preferably, X is a substituted or unsubstituted $C_1$–$C_6$ alkyl group. Also, X is preferably unsubstituted. More preferably, X is methyl or ethyl.

Preferably, $R_1$ and $R_2$ each is independently hydrogen, $C_1$–$C_6$ alkyl, hydroxyalkyl, alkylaryl or aralkyl. More preferably, $R_1$ and $R_2$ each is independently hydrogen or $C_1$–$C_2$ alkyl.

In particularly preferred embodiments, A is sulfur or $CH_2$, Z is $CH_2$, and X is methyl.

Preferred examples of compounds of the Formula I include: N-(5-[2-(2-amino-4(3H)-oxo-5,6,7,8-tetrahydropyrido[2,3-d]-pyrimidin-6-yl)ethyl]-4-methylthieno-2-yl)-L-glutamic acid; N-(5-[2-(2-amino-4-oxo-4,6,7,8-tetrahydro-3H-pyrimido[5,4-6][1,4]-thiazin-6-yl)ethyl]-4-methylthieno-2-yl)-L-glutamic acid diethyl ester; and N-(5-[2-(2-amino-4-oxo-4,6,7,8-tetrahydro-3H-pyrimido[5,4-6][1,4]-thiazin-6-yl)ethyl]-4-methylthieno-2-yl)-L-glutamic acid.

The compounds of the Formula I are useful as GARFT inhibitors. The compounds of Formula I in which $R_1$ and $R_2$ are each hydrogen are especially active antitumor or antiproliferative agents. The compounds of Formula I wherein $R_1$ and $R_2$ are each a moiety that forms a readily hydrolyzable ester group with the attached carboxyl, preferably an ethyl group, are useful intermediates for forming the free glutamic acid forms of the compounds and can also be hydrolyzed in vivo and thus act as prodrugs.

The pharmaceutically acceptable salts of the invention include, for example, alkaline metal, alkaline earth metal, other non-toxic metals, and ammonium and substituted ammonium salts of the glutamic acid compounds of the invention. Exemplary salts include sodium, potassium, lithium, calcium, magnesium, pyridinium and substituted pyridinium salts of the free acid compounds.

The compounds of the Formula I can be prepared as described below.

To prepare compounds of the Formula I where Z is $CH_2$, a useful starting material is a compound of the Formula II:

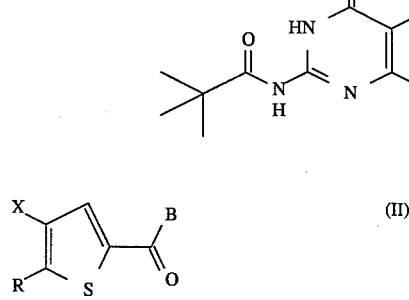

(II)

wherein: R is a halogen, preferably bromo; X is as defined above; and B is OH or an amino acid, preferably diethyl glutamate, linked through the amino portion to form an amide, or a $C_1$–$C_6$ alcohol, preferably a methyl or ethyl alcohol, linked through the alcohol portion to form an ester.

The compound of the Formula II is reacted with a compound of the Formula III:

wherein: Y is $CH_2OH$ or a protected pyridopyrimidine of the Formula IV:

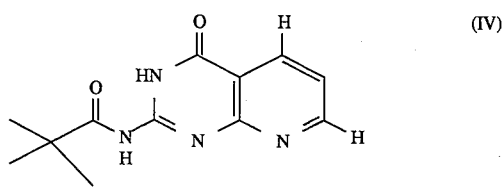

The synthesis then can follow one of two routes, depending on whether Y is a protected pyridopyrimidine or $CH_2OH$.

Where Y is a protected pyridopyrimidine or $CH_2OH$ of the Formula IV, the coupling reaction of compounds of the Formulae II and III is preferably conducted in the presence of a transition metal catalyst, preferably palladium or nickel, in the presence of a base, preferably a non-nucleophilic auxiliary base, in a solvent in which at least one of the reactants is at least partially soluble. Preferred solvents for the coupling reaction of the compounds of Formulae II and III are diethylamine, acetonitrile, dimethylformamide, dimethylacetamide and triethylamine. The basic medium for the coupling reaction is preferably provided via a non-nucleophilic auxiliary base, which is a base capable of neutralizing hydrogen halide acid generated by the coupling reaction. The base is preferably a di- or tri-alkylamine, such as diethylamine, triethylamine or diisopropylethylamine. Where appropriate, a basic solvent can be used instead of a separate solvent and base.

When Y is the pyridopyridimine the coupling reaction of the compounds of Formulae II and III produces a compound of the Formula V:

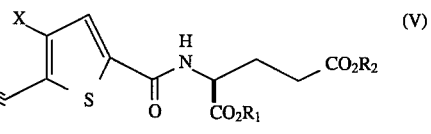

(V)

wherein X, $R_1$ and $R_2$ are as defined above.

The compound of the Formula V is reacted with hydrogen gas, preferably at 45–1000 psi, in the presence of a suitable transition metal catalyst, preferably platinum, palladium or rhodium metal on a carbon or other suitable support, in a suitable solvent, preferably acetic acid or trifluoroacetic acid, to obtain a compound of the Formula VI:

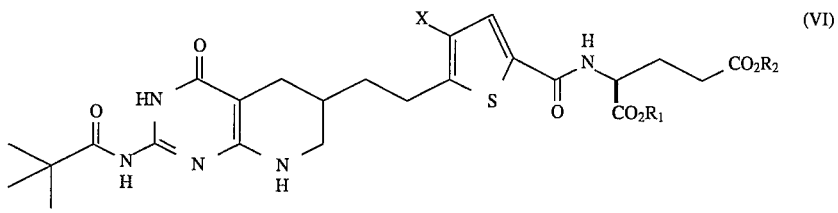

wherein X, $R_1$, and $R_2$ are defined above.

Finally, the compound of Formula VI is hydrolyzed to form a free glutamic acid ($R_1$ and $R_2$ are each H) of Formula I.

Where Y is $CH_2OH$, the reaction of the compounds of Formulae II and III produces a compound of the Formula VII:

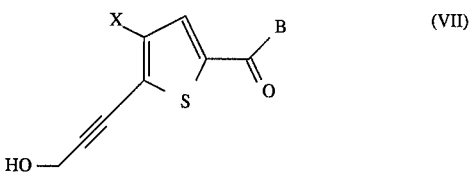

wherein X and B are as defined above.

The compound of the Formula VII is reacted with hydrogen gas in the presence of a suitable metal catalyst, preferably palladium or platinum, to obtain a compound of the Formula VIII:

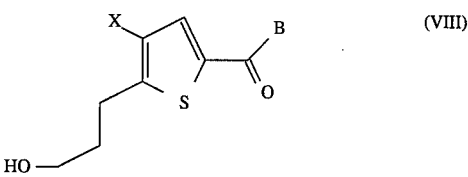

wherein X and B are as defined above.

The compound of the Formula VIII is reacted with an oxidizing agent, preferably tetrapropylammonium perruthenate, to obtain a compound of the Formula IX:

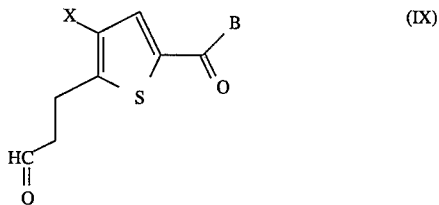

wherein X and B are as defined above.

The compound of the Formula IX is reacted with a methylene transfer reagent, preferable methylene triphenylphosphorane, in a suitable solvent, preferably tetrahydrofuran, to obtain a compound of the Formula X:

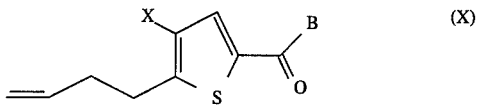

wherein X and B are as defined above.

The compound of the Formula X is reacted with a dihydroxylating agent, preferably osmium tetroxide, in the presence of a suitable oxidizing agent, preferably N-methylmorpholine-N-oxide, to obtain a compound of the Formula XI:

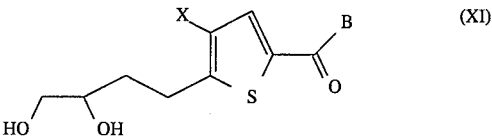

wherein X and B are as defined above.

The compound of the Formula XI is converted to a compound of the Formula I using any of the four processes described below.

In a first conversion process, the compound of the Formula XI is reacted with a sulfonylating agent, preferably p-toluenesulfonyl chloride or methanesulfonyl chloride, in the presence of a non-nucleophilic base, preferably triethylamine or diisopropylethyl amine, to give an intermediate mono-sulfonylated compound. This intermediate is then reacted with a strong base, preferably sodium hydride, to obtain a compound of the Formula XII:

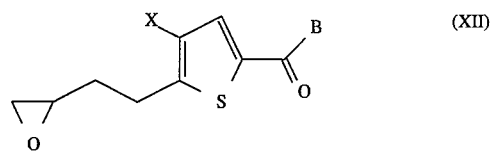

wherein X and B are as defined above.

The epoxide of Formula XII is reacted with a nitrogen containing nucleophile, preferably sodium azide, in the presence of a mild Lewis-acid catalyst, preferably lithium perchlorate or magnesium perchlorate, to obtain an intermediate alcohol azide. Reduction of the alcohol azide, preferably with hydrogen gas in the presence of a metal catalyst, and subsequent protection with a suitable nitrogen-protecting group, preferably t-butoxycarbonyl, benzoxycarbonyl or benzyl, produces a compound of the Formula XIII:

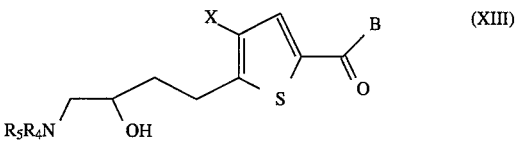

wherein X and B are as defined above, and $R_4$ and $R_5$ are each independently hydrogen or a suitable nitrogen-protecting group. Preferred protecting groups are t-butoxycarbonyl, benzyloxycarbonyl and benzyl.

The compound of the Formula XIII is reacted with an acylating or sulfonylating agent, preferably methanesulfonyl chloride or p-toluenesulfonyl chloride, in the presence of a non-nucleophilic base, preferably triethylamine or diisopropylethylamine, in a suitable solvent in which at least one of the reactants is at least partially soluble, to obtain an activated hydroxy group. The activated hydroxy group is displaced with a suitable nucleophile, preferably a thioacid salt, more preferably potassium thioacetate, to obtain a compound of the Formula XIV:

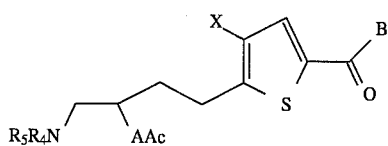

(XIV)

wherein A, X, B, and $R_4$ and $R_5$ are as defined above, and Ac is an acyl group. Preferably, Ac is acetyl.

Alternatively, the compound of the Formula XIII can be converted to the compound of the Formula XIV in one chemical operation using triphenylphosphine, diethyl or dimethyl azadicarboxylate, and an acidic nucleophile, preferably thioacetic acid, in a suitable solvent.

The compound of the Formula XIV is treated with a nucleophilic base, preferably potassium carbonate, sodium carbonate, sodium hydroxide or potassium hydroxide, in an alcoholic solvent, preferably methanol, ethanol or isopropanol, in the presence of an alkylating agent, preferably dimethyl or diethyl chloromalonate, to obtain a compound of the Formula XV:

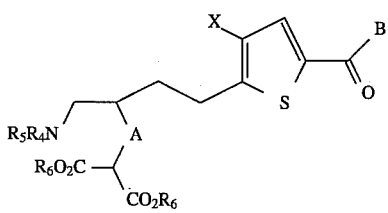

(XV)

wherein A, X, B, and $R_4$ and $R_5$ are as defined above, and each $R_6$ is independently hydrogen or a moiety that forms with the attached $CO_2$ group a readily hydrolyzable ester group. Preferably, $R_6$ is $C_1$–$C_6$ alkyl, hydroxyalkyl, alkylaryl or aralkyl. More preferably, $R_6$ is a $C_1$–$C_2$ alkyl.

The compound of the Formula XV is treated under conditions suitable to remove either $R_4$ or $R_5$, or both protecting groups, to obtain a compound of the Formula XVI:

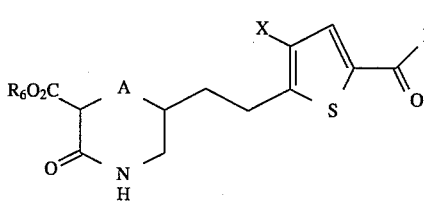

(XVI)

wherein A, X, B and $R_6$ are as defined above. Where t-butoxycarbonyl is used as a protecting group, suitable conditions are treatment with trifluoroacetic acid, followed by neutralization.

The compound of the Formula XVI is reacted with an alkylating agent, preferably trimethyl or triethyl oxonium tetrafluoroborate, in a suitable solvent, preferably dichloromethane, to form an intermediate lactim ether. The intermediate lactim ether is reacted with guanidine in an alcoholic solvent, preferably methanol, ethanol or isopropanol, to form a compound of the Formula XVII:

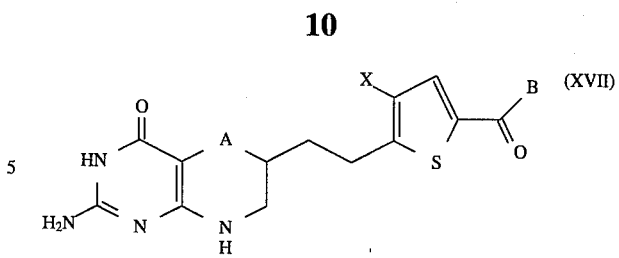

(XVII)

wherein A, X and B are as defined above.

Alternatively, the compound of the Formula XVI can be converted to the compound of the Formula XVII by reacting the compound of the Formula XVI with a thiolating agent, preferably $P_2S_5$ or 2,4-bis(4-methoxyphenyl)-1,3-dithia-2,4-diphosphetane-2,4-disulfide, to form the thiolactam intermediate. This intermediate is then alkylated with an alkylating agent, preferably methyl iodide or trimethyl or triethyl oxonium tetrafluoroborate, and then with guanidine in an alcoholic solvent, preferably methanol, ethanol or isopropanol, to obtain the compound of the Formula XVII.

Where B is an alcohol function—i.e., where the group attached with B forms an ester group—the compound of the Formula XVII is hydrolyzed under basic conditions to form a compound of the Formula XVIII:

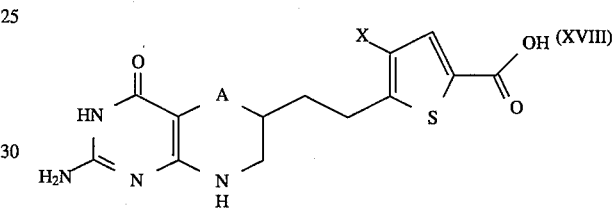

(XVIII)

wherein A and X are as defined above.

The compound of the Formula XVIII is peptide coupled, by means well known to those skilled in the art, with a glutamic acid diester hydrochloride, to form a diester of the Formula XIX:

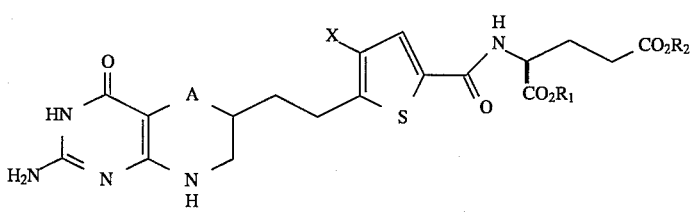

(XIX)

wherein A, X, $R_1$ and $R_2$ are as defined above, except that neither $R_1$ nor $R_2$ is hydrogen.

Finally, if the free glutamic acid form is desired, the compound of the Formula XIX is hydrolyzed to form a compound of the Formula I.

In the second conversion process, a compound of the Formula XIV is prepared as described above. This compound is treated with acid, preferably trifluoroacetic, hydrochloric or p-toluenesulfonic acid, to remove all of the protecting groups ($R_4$, $R_5$ and Ac) to obtain a compound of the Formula XX:

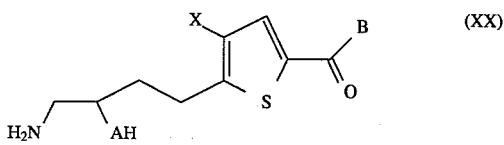

(XX)

wherein A, X and B are as defined above.

The compound of the Formula XX is reacted under weakly basic buffer conditions, preferably using a pH 7 phosphate buffer, in a suitable solvent, preferably ethanol or methanol, with a compound having the Formula XXI:

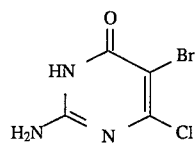 (XXI)

to obtain a compound of the Formula XVII. The remainder of the second process, proceeding from the compound of the Formula XVII to a compound of the Formula I, is conducted in a manner analogous to that described above.

In the third conversion process, the compound of the Formula XI is reacted with a suitable hydroxyl-protecting group, preferably a trialkylsilyl group, more preferably a t-butyldimethylsilyl chloride, in the presence of a mild non-nucleophilic base, preferably triethylamine, to obtain a compound of the Formula XXII:

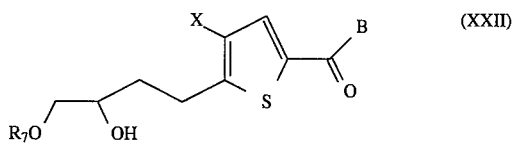 (XXII)

wherein X and B are as defined above, and $R_7$ is a suitable hydroxyl-protecting group, preferably a trialkylsilyl group.

The compound of the Formula XXII is then reacted with an acylating or sulfonylating agent, preferably methansulfonyl chloride or p-toluenesulfonyl chloride, in the presence of a non-nucleophilic base, preferably triethylamine or diisopropylethylamine, in a suitable solvent in which at least one of the reactants is at least partially soluble, to obtain an activated hydroxy group. The activated hydroxy group is displaced with a suitable nucleophile, preferably a thioacid salt, more preferably potassium thioacetate, to obtain a compound of the Formula XXIII:

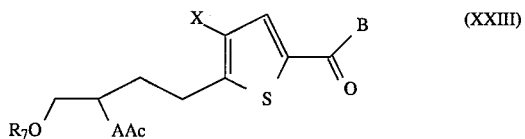 (XXIII)

wherein A, X, B, $R_7$ and Ac are as defined above.

Alternatively, the compound of the Formula XXII can be converted to the compound of the Formula XXIII in one chemical operation using triphenylphosphine or diethyl or dimethyl azadicarboxylate, and an acidic nucleophile, preferably thioacetic acid, in a suitable solvent.

The compound of the Formula XXIII is reacted with a nucleophilic base or a mild acid to selectively remove the acyl group on moiety A. The resulting intermediate is reacted with a compound of the Formula XXIV:

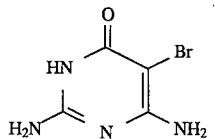 (XXIV)

in the presence of a non-nucleophilic base, preferably triethylamine, diisopropylethylamine or potassium carbonate, to obtain a compound of the Formula XXV:

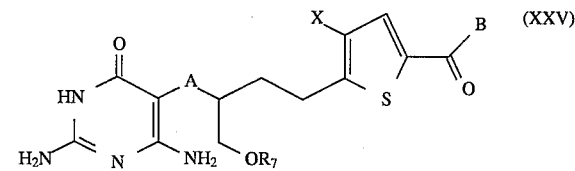 (XXV)

wherein A, X, B and $R_7$ are as defined above.

The protecting group $R_7$ on the compound of the Formula XXV is removed by treatment with a suitable reagent to obtain a compound of the Formula XXVI:

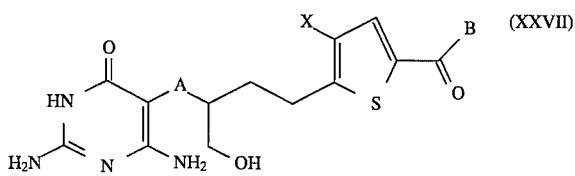 (XXVI)

wherein A, X and B are as defined above. Where $R_7$ is trialkylsilyl, the reagent is preferably a fluoride salt, more preferably potassium fluoride, tetrabutylammonium fluoride or cesium fluoride.

The compound of the Formula XXVI is cyclized to obtain the compound of the Formula XVII by activating the hydroxy group with an activating agent, preferably methanesulfonyl chloride, followed by treatment with a base. Alternatively, the nitrogen of the pyrimidinone is first protected with a suitable protecting group, preferably t-butoxycarbonyl, followed by cyclization and subsequent removal of the protecting group under acidic conditions. The remainder of the process proceeds from the compound of the Formula XVII to a compound of the Formula I in a manner analogous to that described above.

In the fourth and preferred conversion process, an alcohol compound of the Formula XXVI is prepared as described above. This alcohol is reacted with a suitable oxidizing agent to produce an aldehyde functionality that cyclizes to the compound of the Formula XXVII:

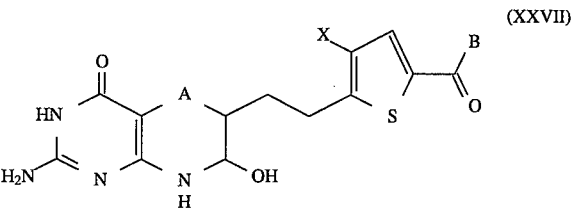 (XXVII)

wherein A, X and B are as defined above.

The compound of the Formula XXVII is reacted with a reducing agent, preferably sodium cyanoborohydride, in the presence of a Lewis acid, preferably boron trifluoride etherate, to obtain a compound of the Formula XVII defined above. The rest of the process proceeds from the compound of the Formula XVII to a compound of the Formula I in a manner analogous to that described above.

The compounds of the Formula I where Z is other than $CH_2$ can be prepared in an analogous manner to those where Z is $CH_2$. In particular, compounds of the Formula I wherein Z is other than $CH_2$ can be prepared using an olefin of the Formula XXXIV:

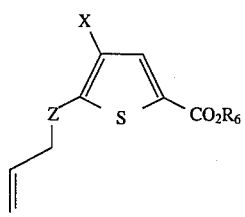

(XXXIV)

wherein X and $R_6$ are as defined above, and Z is as defined above for Formula I except that it is other than $CH_2$.

Where Z is sulfur, oxygen, or a substituted or unsubstituted amino, a compound of the Formula XXXV:

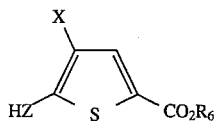

(XXXV)

wherein X and $R_6$ are as defined above, and Z is sulfur, oxygen, or a substituted or unsubstituted amino, is alkylated. The alkylation can be accomplished using an allylhalide, preferably allylbromide, in the presence of a non-nucleophilic base, preferably triethylamine or diisopropylethylamine, to obtain the compound of the Formula XXXIV.

Where Z is a substituted or unsubstituted $C_1$–$C_2$ alkyl other than $CH_2$, a substituted or unsubstituted $C_2$–$C_3$ alkenyl or a substituted or unsubstituted $C_2$–$C_3$ alkynyl, the compound of the Formula XXXIV is prepared by olefination of an aldehyde of the Formula XXXVI:

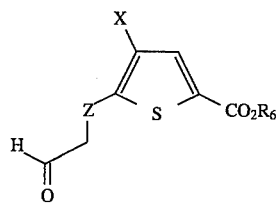

(XXXVI)

wherein X and $R_6$ are as defined above, and Z is a substituted or unsubstituted $C_1$–$C_2$ alkyl other than $CH_2$, a substituted or unsubstituted $C_2$–$C_3$ alkenyl or a substituted or unsubstituted $C_2$–$C_3$ alkynyl. The aldehyde of the Formula XXXVI can be prepared in a manner analogous to that described by Chuan Shih et al., *Journal of Medicinal Chemistry*, vol. 35 (1992), 1109–1116. The olefination of the aldehyde can be accomplished using a methylene transfer agent, preferably methylene-triphenylphosphorane.

The compound of the Formula XXXIV is reacted with a dihydroxylating agent, preferably osmium tetroxide, in the presence of a suitable oxidizing agent, preferably N-methylmorpholine-N-oxide, to obtain a compound of the Formula XXXVII:

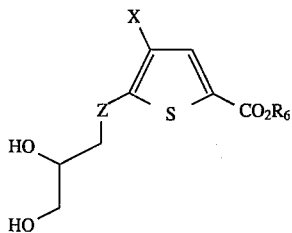

(XXXVII)

wherein X and $R_6$ are as defined above; and Z is as defined above for Formula I, except that it is other than $CH_2$.

The compound of the Formula XXXVII is reacted with a sulfonylating agent, preferably p-toluenesulfonyl chloride or methanesulfonyl chloride, in the presence of a non-nucleophilic base, preferably triethylamine or diisopropylethylamine, to yield an intermediate mono-sulfonylated compound. This intermediate is reacted with a strong base, preferably sodium hydride, to produce a compound of the Formula XXXVIII:

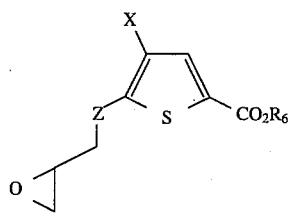

(XXXVIII)

wherein X and $R_6$ are as defined above, and Z is as defined for Formula I except that it is other than $CH_2$.

The epoxide of Formula XXXVIII is reacted with a nitrogen-containing nucleophile, preferably sodium azide, in the presence of a mild Lewis-acid catalyst, preferably lithium or magnesium perchlorate, to an obtain an intermediate alcohol azide. This intermediate is reduced, preferably with hydrogen gas in the presence of a metal catalyst, and subsequent protection with a suitable nitrogen-protecting group, preferably t-butoxycarbonyl, benzoxycarbonyl or benzyl, to produce a compound of the Formula XVII':

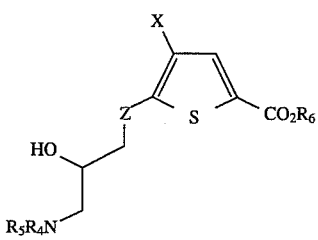

(XVII')

wherein X, $R_6$, and $R_4$ and $R_5$ are as defined above, and Z is as defined for Formula I except that it is other than $CH_2$.

The compound of the Formula XVII' is then reacted with an acylating or sulfonylating agent, preferably methanesulfonyl chloride or p-toluenesulfonyl chloride, in the presence of a non-nucleophilic base, preferably triethylamine or diisopropylethylamine, in a suitable solvent in which at least one of the reactants is at least partially soluble, to obtain an activated hydroxy group. The activated hydroxy group is displaced with a suitable nucleophile, preferably a thioacid salt, more preferably potassium thioacetate, to obtain a compound of the Formula XVIII':

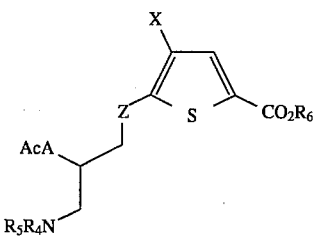

(XVIII')

wherein A, X, $R_6$, $R_4$ and $R_5$, and Ac are as defined above, and Z is as defined for Formula I except that it is other than $CH_2$.

Alternatively, the compound of Formula XVII' is converted to the compound of Formula XVIII' in one chemical operation using triphenylphosphine, diethyl or dimethyl aza-dicarboxylate, and an acidic nucleophile, preferably thioacetic acid, in a suitable solvent.

The compound of the Formula XVIII' is treated with a nucleophilic base, preferably potassium carbonate, sodium carbonate, sodium hydroxide or potassium hydroxide, in an alcoholic solvent, preferably methanol, ethanol or isopropanol, in the presence of an alkylating agent, preferably dimethyl or diethyl chloromalonate, to obtain a compound of the Formula XIX':

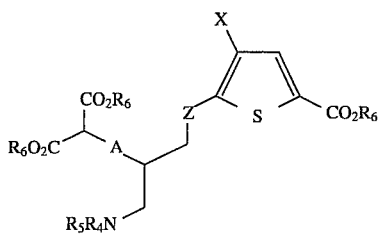
(XIX')

wherein A, X, $R_6$, and $R_4$ and $R_5$ are as defined above, and Z is as defined for Formula I except that it is other than $CH_2$.

The compound of the Formula XIX' is treated under conditions suitable to remove either or both of the $R_4$ and $R_5$ protecting groups to produce a compound of the Formula XX':

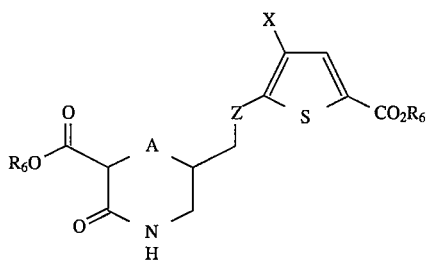
(XX')

wherein A, X and $R_6$ are as defined above, and Z is as defined for Formula I except that it is other than $CH_2$. Where t-butoxycarbonyl is a protecting group, the conditions for removal of this group are preferably treatment with trifluoroacetic acid followed by neutralization to produce the compound of the Formula XX'.

The compound of the Formula XX' is reacted with an alkylating agent, preferably trimethyl or triethyl oxonium tetrafluoroborate, in a suitable solvent, preferably dichloromethane, to form an intermediate lactim ether. The intermediate lactim ether is reacted with guanidine in an alcoholic solvent, preferably methanol, ethanol or isopropanol, to form a compound of the Formula XXI':

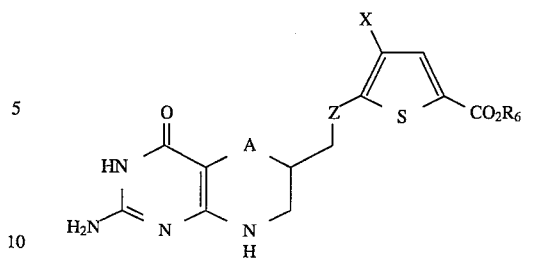
(XXI')

wherein A, X and $R_6$ are as defined above, and Z is as defined for Formula I except that it is other than $CH_2$.

Alternatively, the compound of the Formula XX' is converted to the compound of the Formula XXI' by reacting the compound of the Formula X' with a thiolating agent, preferably $P_2S_5$ or 2,4-bis(4-methoxyphenyl)-1,3-dithia-2,4-diphosphetane-2,4-disulfide to form the thiolactam intermediate. This can then be alkylated with an alkylating agent, preferably methyl iodide or trimethyl or triethyl oxonium tetrafluoroborate, and then with guanidine in an alcoholic solvent, preferably methanol, ethanol or isopropanol, to obtain the compound of the Formula XXI'.

The compound of the Formula XXI' is hydrolyzed under basic conditions to form a compound of the Formula XXII':

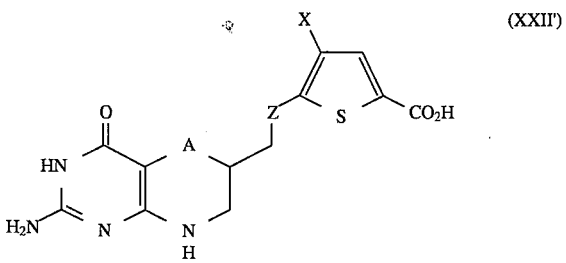
(XXII')

wherein A and X are as defined above, and Z is as defined for Formula I except that it is other than $CH_2$. Where $R_6$ is hydrogen in the compound of the Formula XXI', then the hydrolyzation reaction is not necessary, and the compound of the Formula XXI' is peptide coupled as described below.

The compound of the Formula XXII' (or the compound of the Formula XXI' where $R_6$ is hydrogen), which is in the free carboxylic acid form, can be peptide coupled, by means well known to those skilled in the art, with a glutamic acid diester hydrochloride to form a diester of the Formula XXIII':

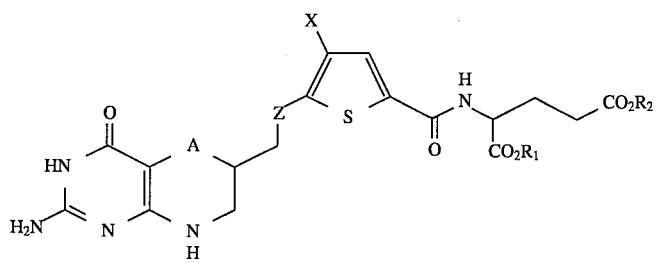
(XXIII')

wherein A, X and are as defined for Formula XXII', and $R_1$ and $R_2$ are each independently a moiety that forms with the attached $CO_2$ a readily hydrolyzable ester group, such as a $C_1-C_6$ alkyl, hydroxyalkyl, alkylaryl or arylalkyl.

Finally, if the free acid form is desired, the compound of the Formula XXIII' is hydrolyzed to produce compounds of the Formula I where $R_1$ and $R_2$ are each H.

A detailed example of the preparation of a compound of the Formula I is provided below.

EXAMPLE 1

N-(5-[2-(2-amino-4(3H)-oxo-5,6,7,8-tetrahydropyrido[2,3-d]pyrimidine-6-yl)ethyl]-4-methylthieno-2-yl)-L-glutamic acid (Compound 1)

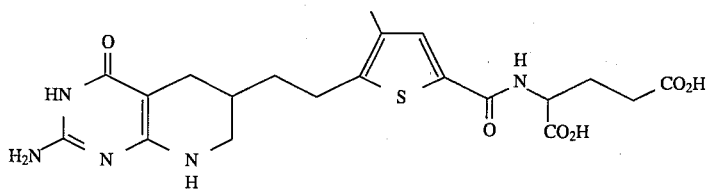

1

Synthesis

Compound 1 was synthesized by the following process.

a. 5-bromo-4-methylthiophene-2-carboxylic acid:

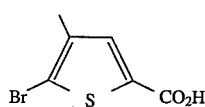

This compound was prepared according to M. Nemec, *Collection Czechoslov. Chem. Commun.*, vol. 39 (1974), 3527.

b. 6-ethynyl-2-(pivaloylamino)-4(3H)-oxopyrido [2,3-d] pyrimidine:

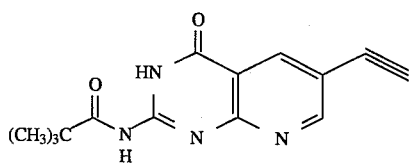

This compound was prepared according to E. C. Taylor & G. S. K. Wong, *J. Org. Chem.*, vol. 54 (1989), 3618.

c. Diethyl N-(5-bromo-4-methylthieno-2-yl)-L-glutamate:

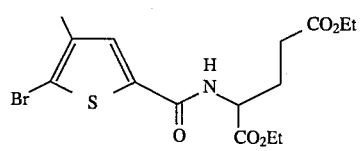

To a stirred solution of 5-bromo-4-methylthiophene-2-carboxylic acid (3.32 g, 15 mmol), 1-hydroxybenzotriazole (2.24 g, 16.6 mmol), L-glutamic acid diethyl ester hydrochloride (3.98 g, 16.6 mmol) and diisopropylethylamine (2.9 ml, 2.15 g, 16.6 mmol) in dimethylformamide (DMF) (40 ml) was added 1-(3-dimethylaminopropyl)-3-ethylcarbodiimide hydrochloride (3.18 g, 16.6 mmol). The resulting solution was stirred under argon at ambient temperature for 18 hours, poured into brine (300 ml), diluted with water (100 ml) and extracted with ether (3×120 ml). The combined organic extracts were washed with water (150 ml), dried over $MgSO_4$ and concentrated in vacuo to give a brown gum, which was purified by flash chromatography. Elution with hexane: EtOAc (2:1) provided the product as an orange oil (5.05 g, 83% yield). Analyses indicated that the product was diethyl N-(5-bromo-4-methylthieno-2-yl) glutamate. NMR(CDCl$_3$) δ: 7.22 (1H, s), 6.86 (1H, d, J=7.5 Hz), 4.69 (1H, ddd, J=4.8, 7.5, 9.4 Hz), 4.23 (2H, q, J=7.1 Hz), 4.12 (2H, q, J=7.1 Hz), 2.55–2.39 (2H, m), 2.35–2.22 (1H, m), 2.19 (3H, s), 2.17–2.04 (1H, m), 1.29 (3H, t, J=7.1 Hz), 1.23 (3H, t, J=7.1 Hz).

Anal. ($C_{15}H_{20}NO_5SBr$) C,H,N,S,Br.

d. diethyl N-(5-[(2-[pivaloylamino]-4(3H)-oxopyrido [2,3-d]pyrimidin-6-yl) ethynyl]-4-methylthieno-2-yl) glutamate:

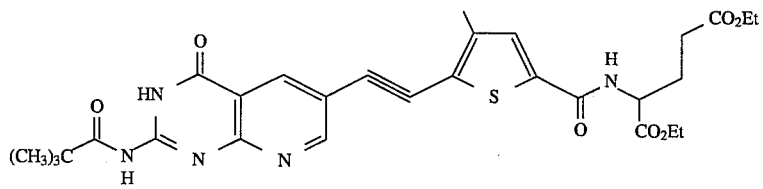

To a stirred solution of diethyl N-(5-bromo-4-methylthieno-2-yl) glutamate (4.21 g, 10.4 mmol) in acetonitrile (55 ml) under an argon atmosphere were added bis (triphenylphosphine) palladium chloride (702 mg, 1.0 mmol), cuprous iodide (200 mg, 1.1 mmol), triethylamine (1.5 ml, 1.09 g, 10.8 mmol) and 6-ethynyl-2-(pivaloylamino)-4(3H)-oxopyrido[2,3-d]pyrimidine (5.68 g, 21 mmol). The resultant suspension was heated at reflux for 6 hours. After cooling to room temperature, the crude reaction mixture was filtered and the precipitate was washed with acetonitrile (50 ml) and ethylacetate (EtOAc) (2×50 ml). The combined filtrates were concentrated in vacuo to give a brown resin, which was purified by flash chromatography. Elution with $CH_2Cl_{12}$: $CH_3OH$ (49:1) provided the product as an orange solid (4.16 g, 67% yield). Analyses indicated that the product was diethyl N-(5-[(2-[pivaloylamino]-4(3H)-oxopyrido [2,3-d]pyrimidin-6-yl) ethynyl]-4-methylthieno-2-yl) glutamate. NMR (CDCl$_3$) δ: 8.95 (1H, d, J=2.2 Hz), 8.59 (1H, d, J=2.2 Hz), 7.33 (1H, s), 7.03 (1H, d, J=7.4 Hz), 4.73 (1H, ddd, J=4.8, 7.4, 9.5 Hz), 4.24 (2H, q, J=7.1 Hz), 4.13 (2H, q, J=7.1 Hz), 2.55–2.41 (2H, m), 2.38 (3H, s), 2.35–2.24 (1H, m), 2.19–2.05 (1H, m), 1.34 (9H, s), 1.30 (3H, t, J=7.1 Hz), 1.24 (3H, t, J=7.1 Hz).

Anal. ($C_{29}H_{33}N_5O_7S.0.75H_2O$) C,H,N,S.

e. diethyl N-(5-[(2-[pivaloylamino]-4(3H)-oxopyrido [2,3,d]pyrimidin-6-yl)ethyl]-4-methylthieno-2-yl) glutamate:

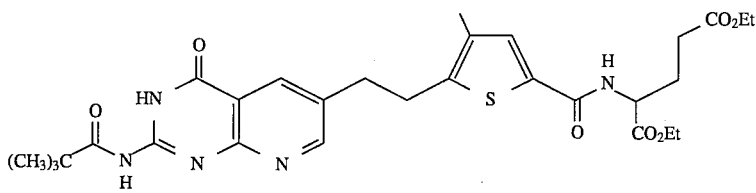

A suspension of diethyl N-(5-[(2-[pivaloylamino]-4(3H)-oxopyrido[2,3-d]pyrimidin-6-yl)ethyl]-4-methylthieno-2-yl) glutamate (959 mg, 1.6 mmol) and 10% Pd on carbon (1.5 g, 150% wt. eq.) in trifluoroacetic acid (30 ml) was shaken under 50 psi of $H_2$ for 22 hours. The crude reaction mixture was diluted with $CH_2C_2$, filtered through a pad of Celite (diatomaceous earth) and concentrated in vacuo. The residue obtained was dissolved in $CH_2Cl_2$ (120 ml), washed with saturated $NaHCO_3$ (2×100 ml), dried over $Na_2SO_4$ and concentrated in vacuo to give a brown gum, which was purified by flash chromatography. Elution with $CH_2Cl_2$:$CH_3OH$ (49:1) provided the product as a yellow solid (772 mg, 80% yield). Analyses indicated that the product was diethyl N-(5-[(2-[pivaloylamino]-4(3H)-oxopyrido[2,3-d]pyrimidin-6-yl)ethyl]-4-methylthieno-2-yl) glutamate. NMR ($CDCl_3$) δ: 8.60 (1H, d, J=2.2 Hz), 8.49 (1H, broad), 8.32 (1H, d, J=2.2 Hz), 7.22 (1H, s), 6.78 (1H, d, J=7.5 Hz), 4.72 (1H, ddd, J=4.8, 7.5, 9.5 Hz), 4.23 (2H, q, J=7.1 Hz), 4.11 (2H, q, J=7.1 Hz), 3.12–3.00 (4H, m), 2.52–2.41 (2H, m), 2.37–2.22 (1H, m), 2.16–2.04 (1H, m), 2.02 (3H, s), 1.33 (9H, s), 1.29 (3H, t, J=7.1 Hz), 1.23 (3H, t, J=7.1 Hz). Anal. ($C_{29}H_{37}N_5O_7S.0.5H_2O$) C,H,N,S.

f. diethyl N-(5-[(2-[pivaloylamino]-4(3H)-oxo-5,6,7,8-tetrahydropyrido[2,3-d]pyrimidin-6-yl)ethyl]-4-methylthieno-2-yl) glutamate:

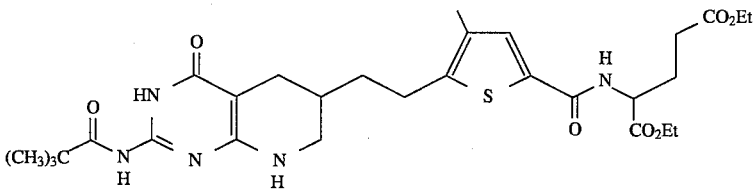

A suspension of diethyl N-(5-[(2-[pivaloylamino]-4(3H)-oxopyrido[2,3-d]pyrimidin-6-yl)ethyl]-4-methylthieno-2-yl) glutamate (2.98 g, 5 mmol), 10% Pt on carbon (1.5 g, 50% wt. eq.) and $PtO_2$ (1.5 g, 50% wt. eq.) in trifluoroacetic acid (170 ml) was shaken under 800 psi of $H_2$ for 40 hours. The crude reaction mixture was diluted with $CH_2Cl_2$, filtered through a pad of Celite, and concentrated in vacuo. The residue obtained was dissolved in $CH_2Cl_2$ (150 ml), washed with saturated $NaHCO_3$ (2×150 ml), dried over $Na_2SO_4$, and concentrated in vacuo to give a brown resin, which was purified by flash chromatography. Elution with $CH_2Cl_2$; $CH_3$ OH (24:1) provided initially an unreacted substrate (1.42 g, 48% yield) and then the product as a yellow solid (293 mg, 10% yield). Analyses indicated that the product was diethyl N-(5-[(2-[pivaloylamino]-4(3H)-oxo-5,6,7,8-tetrahydropyrido-[2,3-d]pyrimidin-6-yl)ethyl]-4-methylthieno-2-yl) glutamate. NMR ($CDCl_3$) δ: 7.24 (1H, s), 6.75 (1H, d, J=7.6 Hz), 5.57 (1H, broad) , 4.72 (1H, ddd, J=4.8, 7.6, 12.6 Hz), 4.22 (2H, q, J=7.1 Hz), 4.11 (2H, q, J=7.1 Hz), 3.43–3.36 (1H, m), 3.06–2.98 (1H, m), 2.89–2.68 (3H, m), 2.52–2.40 (3H, m), 2.37–2.23 (1H, m), 2.15 (3H, s), 2.14–2.03 (1H, m), 1.94–1.83 (1H, m), 1.73–1.63 (2H, m), 1.32 (9H,s), 1.29 (3H, t, J=7.1 Hz), 1.23 (3H, t, J=7.1 Hz). Anal. ($C_{29}H_{41}N_5O_7S.0.5H_2O$) C,H,N,S.

g. N-(5-[2-(2-amino-4(3H)-oxo-5,6,7,8-tetrahydropyrido-[2,3-d]pyrimidin-6-yl)ethyl]-4-methylthieno-2-yl) glutamic acid (Compound 1):

A solution of diethyl N-(5-[(2-[pivaloylamino]-4(3H)-oxo-5,6,7,8-tetrahydropyrido[2,3-d]pyrimidin-6-yl)ethyl]-4-methylthieno-2-yl) glutamate (293 mg, 0.5 mmol) in 1N NaOH (25 ml) was stirred at ambient temperature for 90 hours, then neutralized with 6N HCl. The precipitate that formed was collected by filtration and washed with water (4×10 ml) to provide the product as a yellow solid (63 mg, 28% yield). Analyses indicated that the product was N-(5-[2-(2-amino-4(3H)-oxo-5,6,7,8-tetrahydropyrido[2,3-d]pyrimidin-6-yl)ethyl]-4-methylthieno-2-yl) glutamic acid. NMR (DMSO-d6) δ: 12.44 (2H, broad), 9.89 (1H, broad), 8.42 (1H, d, J=7.8 Hz), 7.57 (1H, s), 6.39 (1H, br s), 6.12 (2H, br s), 4.30 (1H, ddd, J=4.8, 7.8, 9.6 Hz), 3.26–3.18 (2H, m), 2.83–2.74 (3H, m), 2.31 (2H, t, J=7.4 Hz), 2.12 (3H, s), 2.09–2.01 (1H, m), 1.94–1.80 (2H, m), 1.68–1.47 (3H,m). Anal. ($C_{20}H_{25}N_5O_6S.1.1H_2O$) C,H,N,S.

Biological and Biochemical Evaluation

Determination of Inhibition Constants for GAR Transformylase:

The GAR-transformylase (GARFT) assay method of Young et al., *Biochemistry* 23 (1984), 3979–3986, was modified and used as described below. Reactions mixtures contained the catalytic domain of the human GARFT, 0–250 nM of the test compound, 20 μM glycinamide ribonucleotide (GAR), 10 or 20 μM $N^{10}$-formyl-5,8-dideazafolate (FDDF), 50 mM HEPES-KOH (pH 7.5), and 50 mM KCl. The reaction was initiated with the addition of enzyme to a final concentration of 11 nM, followed by monitoring of the increase in absorbance at 294 nm at 20° C. ($e_{294}$=18.9 mM$^{-1}$ cm$^{-1}$).

The GARFT inhibition constant ($K_i$) was determined from the dependence of the steady-state catalytic rate on inhibitor and substrate concentration. The type of inhibition observed was determined to be competitive with respect to FDDF by the dependence of the apparent $K_i$ ($K_{i,app}$) on the concentration of FDDF and was shown to be described by $K_{i,app}$=$K_i$+($K_i/K_m$)[FDDF]. The Michaelis constant for FDDF, $K_m$, was determined independently by the dependence of the catalytic rate on FDDF concentration. Data for both the $K_m$ and $K_i$ determinations were fitted by non-linear methods to the Michaelis equation, or to the Michaelis equation for competitive inhibition, as appropriate. Data resulting from tight-binding inhibition was analyzed and $K_i$ was determined by fitting the data to the tight-binding equation of Morrison, *Biochem Biophys Acta* 185 (1969), 269–286, by nonlinear methods.

Determination of Dissociation Constants for Human Folate Binding Protein:

The dissociation constant (Kd) for human folate-binding protein (FBP) was determined in a competitive binding assay using membrane associated FBP prepared from cultured KB cells. Preparation of KB cell Membrane Fraction:

Adherent KB cells were scraped from flasks, washed once in ice-cold PBS, and centrifuged at 5000× g for 5 minutes at 4° C. Pelleted cells ($2 \times 10^8$ cells) were resuspended in 10 ml of suspension buffer ($KH_2PO_4$-KOH pH 7.4:10 mM EDTA: 10 mM 2-mercaptoethanol), sonicated briefly to complete cell lysis and centrifuged at 12000× g for 10 minutes at 4° C. The pellet was stripped of endogenous bound folate by resuspension in 20 ml of acidic buffer (50 mM $KH_2PO_4$-KOH pH 3.5:10 mM EDTA: 10 mM 2-mercaptoethanol) and centrifuged as before. The pellet was then resuspended in 20 ml of the suspension buffer at pH 7.4 and centrifuged as before. The pellet was resuspended in 5 ml of suspension buffer at pH 7.4 lacking EDTA. Protein content was quantitated using the Bradford method with BSA as standard. Typical yields for this procedure were 4–5 mg total membrane protein per $2 \times 10^8$ cells. This final suspension was used as a source of membrane-associated human FBP. FBP Competitive Binding Assay:

Inhibitor was allowed to compete against $^3$H-folic acid for binding to FBP. Reactions mixtures contained 50–100 mg of cell membrane protein containing 3–6 pmoles (3–6 nM) of FBP, 17.25 pmoles $^3$H-folic acid (17.25 nM, 0.5 μCi), various concentrations of competitor, in 1 ml of 50 mM KH₂PO4-KOH pH 7.4 : 10 mM 2-mercaptoethanol. Reactions were performed at 25° C. Because of the very slow release of bound $^3$H-folic acid, the competitor was prebound for 30 minutes in the absence of $^3$H-folic acid. $^3$H-Folic acid was then added and the mixtures were allowed to equilibrate for 2.5 hours. The full reaction mixtures were drawn through nitrocellulose filters under vacuum to trap the cell membranes with bound $^3$H-folic acid. The trapped membranes were then washed 4 times with 1 ml of reaction buffer. The amount of bound $^3$H-folic acid was measured by scintillation counting of the nitrocellulose membrane. The data obtained were nonlinearly fitted as described above. The FBP $K_d$ for $^3$H-folic acid, used to calculate the competitor $K_d$, was obtained by direct titration of FBP with $^3$H-folate and subsequent nonlinear fitting of the data to a tight-binding $K_d$ equation.

Cell lines:

The cell lines used and their origin are tabulated in Table 1. The growth conditions and media requirements of each cell line are summarized in Table 2. All cultures were maintained at 37° C., 5% air-$CO_2$ in a humidified incubator.

In vitro growth inhibition:

Stock solutions of the inhibitors were prepared in 10 mM sodium bicarbonate in water and stored in 1 ml aliquots at −20° C. for cell culture experiments. Cell-growth inhibition was measured by a modification of the method of Mosmann, *J. Immunol. Methods* 65 (1983), 55–63.

Mid-log phase cells of each cell line were diluted to 18,500 cells/ml in fresh RPMI growth medium (Mediatech, Washington, D.C.) supplemented with dialyzed fetal-calf serum (Hyclone Laboratories Inc., Logan, Utah), and then aliquoted into columns 2 through 12 of 96-well microtiter plates. Column 1 was filled with the same volume, 135 ml, of fresh medium, without cells, for use as a blank. The plates were then placed in a 37° C., 5% air-$CO_2$ incubator. After 1 to 4 hours, plates were removed from the incubator followed by addition of the test compound at 10× final concentration, 15 ml/well in binary dilutions, to columns 12 to 4. For reversal experiments, hypoxanthine (1.75 mM) or AICA (1.75 mM) was included in all drug solutions (final concentration 175 mM). Wells containing each concentration of test compound were prepared in quadruplicate on each plate. Fifteen milliliters of media, without test compound, were added to the wells in column 1 of the plates. The cells were then returned to the incubator and remained undisturbed for the full incubation period. On day 3 for L1210 and L1210/CI920 cells or day 5 for CCRF-CEM cells, 50 ml of 0.8 mg/ml MTT (4,5-dimethylthiazol-2-yl)-2,5-diphenyl tetrazolium bromide; Sigma catalog no. M2128) dissolved in tissue culture medium was added to each well of all plates, after which cells were returned to the incubator. After 4 hours, all plates were removed from the incubator and centrifuged at 1200 rpm for 7 minutes. Media were siphoned off and 150 ml of DMSO was added to each well of all plates. Plates were then mixed at slow speed on a vortex mixer for 1 hour in the dark at room temperature. The extent of metabolized MTT was measured spectrophotometrically at 540 nm on a Molecular Devices Vmax™ kinetic microplate reader. The concentration of drug required to reduce cell growth by 50% as measured by MTT metabolism was determined by interpolation between the O.D. (minus blank) immediately above and below 50% of control O.D. (minus blank).

TABLE 1

Tissue of Origin and Source of Cell Lines Employed in In Vitro Studies

| Cell Line | Source | Origin |
| --- | --- | --- |
| L1210 | ATCC[#] | Mouse, lymphocytic leukemia |
| CCRF-CEM | ATCC[#] | Human, acute lymphoblastic leukemia |

[#]ATCC = American Type Culture Collection

TABLE 2

Culture Conditions, Plating Densities and Incubation Times Used in Microtiter Assays

| Cell line | Medium | DFCS Conc.* (%) | Plating Density (cells/well) | Incubation Time (days) |
| --- | --- | --- | --- | --- |
| L1210 | RPMI-1640 | 5 | 2500 | 3 |
| CCRF-CEM | RPMI-1640 | 10 | 2500 | 5 |

*DFCS Conc. = dialyzed fetal calf serum concentration.

TABLE 3

Comparative Data for Test Compound and 6R-DDATHF Growth Inhibition Using Continuous (72-hour) Exposure

| Compound | GARFT $K_i$ (nM) | $IC_{50}$ Cell Culture L1210 (nM)[a] | $IC_{50}$ Cell Culture CCRF-CEM (nM)[a] | Human Folate Binding Protein $K_d$ (nM) |
| --- | --- | --- | --- | --- |
| 1 | 1.4 | 13.5 | 6.1 | 28 |
| DDATHF[b] | 25 | 17.5 | 1.5 | 0.020 |

[a]: Mean $IC_{50}$ ± standard deviation;
[b]: 6R-DDATHF, the 6R diastereomer of 5,,10-dideazatetrahydrofolic acid (Lometrexol) (See F.M. Muggia, "Folate antimetabolites inhibitor to de novo purine synthesis," New Drugs, Concepts and Results in Cancer Chemotherapy, Kluwer Academic Publishers, Boston (1992), 65–87.

As the above comparative data show, Compound 1 has a relative folate binding protein $K_d$ that is about 1400 times less potent than 6R-DDATHF.

EXAMPLE 2

N-(5-[2-(2-amino-4-oxo-4,6,7,8-tetrahydro-3H-pyrimido[5,4-6]-[1,4]thiazin-6-yl)ethyl]-4-methylthieno-2-yl)-L-glutamic acid (Compound 2)

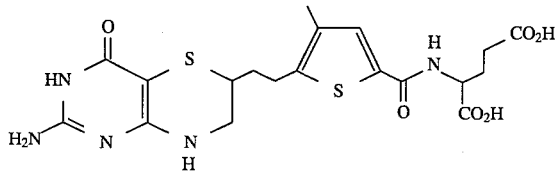

Compound 2 was prepared as follows.

a. methyl 5-bromo-4-methylthiophene-2-carboxylate:

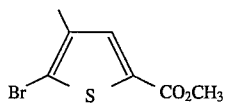

To a solution of 5-bromo-4-methylthiophene-2-carboxylic acid (20.32 g, 92 mmol) in $CH_3OH$ (450 ml) was added concentrated $H_2SO_4$ (4 ml). The resultant solution was heated at reflux for 18 hours. The solvent was removed by concentration in vacuo, and the residue obtained was partitioned between saturated $NaHCO_3$ (350 ml) and ether (350 ml). The layers were separated and the aqueous phase extracted with ether (3×150 ml). The combined organic extracts were dried over $MgSO_4$ and concentrated in vacuo to give a red oil, which was purified by flash chromatography. Elution with hexane:ethyl acetate (9:1) provided the product as a yellow oil, which solidified on standing (18.34 g, 85% yield). Analyses indicated that the product was methyl 5-bromo-4-methylthiophene-2-carboxylate. NMR ($CDCl_3$) δ: 7.47 (1H, s), 3.86 ($^3$H, s), 2.20 ($^3$H, s). Anal. ($C_7H_7O_2SBr$) C,H,S,Br.

b. methyl 5-(3-hydroxypropynyl)-4-methylthiophene-2-carboxylate:

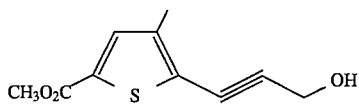

To a stirred solution of methyl 5-bromo-4-methylthiophene-2-carboxylate (5.18 g, 22 mmol) in diethylamine (60 ml) under an argon atmosphere were added bis(triphenylphosphine) palladium chloride (77 mg, 0.11 mmol), cuprous iodide (42 mg, 0.22 mmol) and propargyl alcohol (1.5 ml, 1.44 g, 26 mmol). The resultant mixture was stirred at ambient temperature for 18 hours. The solvent was removed by concentration in vacuo, and the residue obtained was diluted with water (200 ml) and then extracted with EtOAc (3×100 ml). The combined organic extracts were washed with 0.5 N HCl (100 ml), dried over $MgSO_4$ and concentrated in vacuo to give a brown oil, which was purified by flash chromatography. Elution with hexane:EtOAc (2:1) provided the product as an orange oil, which solidified on standing (4.07 g, 88% yield). Analyses indicated that the product was methyl 5-(3-hydroxypropynyl)-4-methylthiophene-2-carboxylate. NMR ($CDCl_3$) δ: 7.52 (1H, s), 4.55 (2H, s), 3.87 (3H, s), 2.29 (3H, s). Anal. ($C_{10}H_{10}O_3S$) C,H,S.

c. methyl 5-(3-hydroxypropyl)-4-methylthiophene-2-carboxylate:

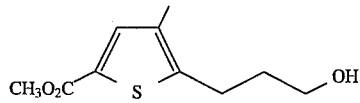

A suspension of methyl 5-(3-hydroxypropynyl)-4-methylthiophene-2-carboxylate (3.86 g, 18 mmol) and 5% Pd on carbon (0.72 g, 19% wt. eq.) in EtOAc (110 ml) was shaken under 50 psi of $H_2$ for 20 hours. The crude reaction mixture was filtered through a pad of Celite, and the filtrate was concentrated in vacuo to provide the product as a yellow oil (3.84 g, 98% yield). Analyses indicated that the product was methyl 5-(3-hydroxypropyl)-4-methylthiophene-2-carboxylate. NMR ($CDCl_5$) δ: 7.51 (1H, s), 3.84 (3H, s), 3.71 (2H, t, J=6.2 Hz), 2.86 (2H, t, J=7.6 Hz), 2.16 (3H, s), 1.92 (2H, tt, J=6.2, 7.6 Hz). Anal. ($C_{10}H_{14}O_3S$) C,H,S.

d. methyl 4-methyl-5-(3-oxopropyl) thiophene-2-carboxylate:

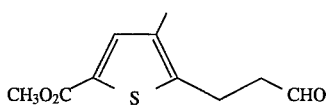

To a stirred suspension of methyl 5-(3-hydroxypropyl)-4-methylthiophene-2-carboxylate (3.74 g, 17 mmol), N-methylmorpholine-N-oxide (3.00 g, 26 mmol) and powdered 4Å molecular sieves (4.5 g) in $CH_2Cl_2$ (50 ml) was added tetrapropylammonium perruthenate (300 mg, 0.85 mmol). The resultant suspension was stirred at ambient temperature for 40 minutes. The solvent was removed by concentration in vacuo, and the residue obtained was purified by flash chromatography. Elution with hexane:EtOAc (4:1) provided the product as a yellow oil (1.82 g, 49% yield) Analyses indicated that the product was methyl 4-methyl-5-(3-oxopropyl) thiophene-2-carboxylate. NMR ($CDCl_3$) δ: 9.83 (1H, t, J=0.8 Hz), 7.50 (1H, s), 3.84 (3H, s), 3.07 (2H, t, J=7.4 Hz), 2.83 (2H, dt, J=0.8, 7.4 Hz), 2.17 (3H, s). Anal. ($C_{10}H_{12}O_3S$) C,H,S e. methyl 5-(3-butenyl)-4-methylthiophene-2-carboxylate:

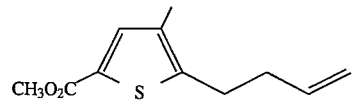

To a stirred suspension of methyltriphenylphosphonium bromide (3.14 g, 8.8 mmol) in THF (30 ml) under an argon atmosphere at 0° C. was added 2.5M n-butyllithium in hexane (3.4 ml, 8.5 mmol). The resultant slurry was stirred for 10 minutes at 0° C., for 75 minutes at ambient temperature, and then cooled to −65° C. prior to the dropwise addition of a solution of the methyl 4-methyl-5(3-oxopropyl) thiophene-2-carboxylate (1.71 g, 8.1 mmol) in THF (30 ml). The cooling bath was removed and the reaction was stirred for 90 minutes while gradually warming to room temperature. The crude reaction mixture was concentrated in vacuo to a volume of 20 ml, diluted with ether (200 ml), and filtered through a pad of celite. The filtrate was concentrated in vacuo to give an orange oil, which was purified by flash chromatography. Elution with hexane:EtOAc (95:5) provided the product as a yellow oil (772 mg, 46%). Analyses indicated that the product was methyl 5-(3-butenyl)-4-methylthiophene-2-carboxylate. NMR ($CDCl_3$) δ: 7.50 (1H, s), 5.84 (1H, ddt, J=10.2, 17.0, 6.6 Hz), 5.07 (1H, dd, J=1.6, 17.0 Hz), 5.02 (1H, dd, J=1.6, 10.2 Hz), 3.84 ($^3$H, s). Anal. ($C_{11}H_{14}O_2$) C,H,S.

f. methyl 5-(3,4-dihydroxybutyl)-4-methylthiophene-2-carboxylate:

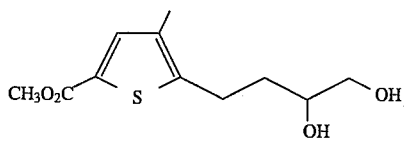

To a stirred solution of N-methylmorpholine-N-oxide (735 mg, 6.3 mmol) and osmium tetroxide (5 mg, 0.02 mmol) in acetone (30 ml) was added a solution of methyl 5-(3-butenyl)-4-methylthiophene-2-carboxylate (701 mg, 3.3 mmol) in acetone (20 ml). The resultant solution was stirred under an argon atmosphere at ambient temperature for 48 hours, then filtered through a pad of Celite. The filtrate was acidified by addition of 0.5M $H_2SO_4$ (10 ml), and the acetone was removed by concentration in vacuo. The aqueous residue was diluted with water (20 ml) and extracted with EtOAc (3×25 ml). The combined organic extracts were washed with water (3×25 ml), dried over $Na_2SO_4$, and concentrated in vacuo to give a brown gum, which was purified by flash chromatography. Elution with $CH_2Cl_2$; EtOAc (2:3) provided the product as an off-white solid (577 mg, 71% yield). Analyses indicated that the product was methyl 5-(3,4-dihydroxybutyl)-4-methylthiophene-2-carboxylate. NMR (CDCl$_3$) δ: 7.50 (1H, s), 3.84 ($^3$H, s), 3.79–3.72 (1H, m), 3.86 (1H, dd, J=3.2, 10.9 Hz), 3.48 (1H, dd, J=7.4, 10.9 Hz), 3.00–2.80 (2H, m). Anal. ($C_{11}H_{16}O_4S$) C,H,S.

The above examples are given to illustrate various aspects of the invention. It is to be understood that appropriate modifications will be within the capabilities of one having ordinary skill in the art in light of the teachings contained herein.

Where possible as a matter of chemistry, chemical groups recited herein can be substituted. In some cases, this possibility is made explicit by reciting, e.g., substituted or unsubstituted $C_1$–$C_3$ alkyl group.

Where more than one $R_6$ group is recited in any Formula herein, each $R_6$ can be independently selected from the possibilities given.

What is claimed is:

1. A compound of the formula II:

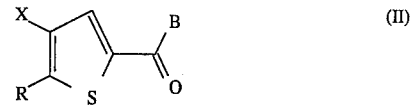

wherein:

R is a halogen;

X is a substituted or unsubstituted $C_1$–$C_6$ alkyl group; and

B is glutamic acid or a derivative thereof, linked through the amino portion to form an amide.

2. A compound according to claim 1, wherein R is bromo.

3. A compound according to claim 1, wherein when X is substituted, the substituents are selected from OH, $NH_2$, O-methyl, O-ethyl, SH, $SCH_3$ and NH-methyl.

4. A compound according to claim 1, wherein X is unsubstituted.

5. A compound according to claim 4, wherein X is methyl or ethyl.

6. A compound according to claim 1, wherein B is diethyl glutamate.

7. A compound of the formula VII:

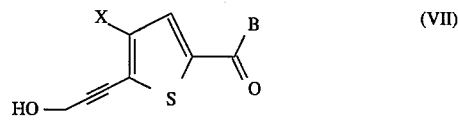

wherein:

X is a substituted or unsubstituted $C_1$–$C_6$ alkyl group; and

B is glutamic acid or a derivative thereof, linked through the amino portion to form an amide.

8. A compound according to claim 7, wherein when X is substituted, the substituents are selected from OH, $NH_2$, O-methyl, O-ethyl, SH, $SCH_3$ and NH-methyl.

9. A compound according to claim 7, wherein X is unsubstituted.

10. A compound according to claim 9, wherein X is methyl or ethyl.

11. A compound according to claim 7, wherein B is diethyl glutamate.

* * * * *